(12) United States Patent
Palmer

(10) Patent No.: US 6,537,242 B1
(45) Date of Patent: Mar. 25, 2003

(54) METHOD AND APPARATUS FOR ENHANCING PENETRATION OF A MEMBER FOR THE INTRADERMAL SAMPLING OR ADMINISTRATION OF A SUBSTANCE

(75) Inventor: Phyllis J. Palmer, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 145 days.

(21) Appl. No.: 09/588,767

(22) Filed: Jun. 6, 2000

(51) Int. Cl.[7] ............................................... A61B 17/20
(52) U.S. Cl. .................. 604/22; 604/191; 600/309; 600/583
(58) Field of Search ........................ 604/22, 191, 181, 604/183, 200, 207, 272; 606/181, 184–186, 172, 189; 600/309, 583; 422/57

(56) References Cited

U.S. PATENT DOCUMENTS

| | | | |
|---|---|---|---|
| 3,963,441 A | * | 6/1976 | Dietrich ....................... 422/57 |
| 4,695,273 A | | 9/1987 | Brown |
| 5,250,023 A | | 10/1993 | Lee et al. |
| 5,873,856 A | | 2/1999 | Hjertman et al. |
| 5,879,326 A | | 3/1999 | Godshall et al. |
| 6,183,489 B1 | * | 2/2001 | Douglas et al. ............. 600/583 |
| 6,332,875 B2 | | 12/2001 | Inkpen et al. |
| 6,334,856 B1 | * | 1/2002 | Allen et al. .................. 604/191 |
| 6,349,229 B1 | * | 2/2002 | Watanabe et al. ........... 600/309 |

FOREIGN PATENT DOCUMENTS

| | | |
|---|---|---|
| CA | 2229522 | 4/1998 |
| FR | 2 612 401 A1 | 9/1988 |
| GB | 1 216 813 | 12/1970 |
| JP | 04246364 A * | 9/1992 |
| WO | WO 97/48440 | 12/1997 |
| WO | WO 99/34850 | 7/1999 |
| WO | WO 00/74763 A2 | 12/2000 |
| WO | WO 01/41863 A1 | 6/2001 |

* cited by examiner

Primary Examiner—Thomas Denion
Assistant Examiner—Thai-Ba Trieu
(74) Attorney, Agent, or Firm—Venable

(57) ABSTRACT

A device for monitoring, sampling or delivering a substance to the skin of a patient includes a medical device and a stretching device for stretching the skin to enhance the contact by the medical device. The medical device generally includes at least a skin penetrating member, such as a cannula. The cannula can be a single needle or an array of microneedles. The method for monitoring, sampling or delivering a substance positions the device on the skin and presses downwardly on the device causing the stretching device to stretch the skin in a target area of the skin penetrating member to enable uniform penetration of the skin. The uniform penetration provides for a more uniform monitoring, sampling or delivery of the substance to the patient.

37 Claims, 6 Drawing Sheets

METHOD AND APPARATUS FOR ENHANCING PENETRATION OF A MEMBER FOR THE INTRADERMAL SAMPLING OR ADMINISTRATION OF A SUBSTANCE

FIELD OF THE INVENTION

The present invention relates to a method and apparatus for monitoring, sampling or delivering a substance. More particularly, the invention is directed to a method and apparatus for applying tension to the skin of a patient to enhance the penetration of a penetrating device in a target site of a patient for monitoring, sampling or delivering.

BACKGROUND OF THE INVENTION

Various devices have been proposed for monitoring, sampling and delivering substances transdermally. Although the prior subcutaneous delivery methods using a needle cannula for delivering pharmaceutical agents and drugs are effective for many applications, the pain normally induced by the needle cannula has prompted the development of less painful delivery methods. Transdermal delivery is one method of avoiding the pain caused by subcutaneous sampling and delivery using a needle cannula.

In recent years there has been an increased interest in microneedles for the sampling of components and for the transdermal delivery of drugs and other substances. Microneedles are micron size needles that can pierce the skin to a depth where a substance can be delivered into the epidermis so that the substance can be absorbed by the body. An advantage of the use of microneedles is the ability to penetrate the outermost layers of the skin with only minor discomfort to the patient compared to a standard needle.

The skin is made up of several layers with the upper composite layer being the epithelial layer. The outermost layer of the skin is the stratum corneum, which has well known barrier properties to prevent molecules and various substances, including most pharmaceutical agents, from entering the body and analytes from exiting the body. The stratum corneum is a complex structure of compacted keratinized cell remnants having a thickness of about 10-30 microns.

Various methods of delivering drugs through the skin form micropores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

Microneedles have been used with some success for various substances that are effective when delivered transdermally or intradermally. However, many of the prior microneedle devices that are currently available are not able to penetrate the skin uniformly across the microneedle surface thereby reducing the surface area available for delivery of the substance. The skin is generally elastic so that the skin deforms before the microneedles penetrate the skin. In some instances, the microneedles deform the skin but do not penetrate the skin to a depth sufficient to deliver a drug. Accordingly, there is a continuing need for improved microneedle devices.

Numerous methods and devices have been proposed to enhance the permeability of the skin and to increase the diffusion of various drugs through the skin so that the drugs can be utilized by the body. Typically, the delivery of drugs through the skin is enhanced by either increasing the permeability of the skin or increasing the force or energy used to direct the drug through the skin.

Sonic, and particularly ultrasonic energy, has been used to increase the diffusion of drugs through the skin. The sonic energy is typically generated by passing an electrical current through a piezoelectric crystal or other suitable electromechanical device. Although numerous efforts to enhance drug delivery using sonic energy have been proposed, the results generally show a low rate of drug delivery.

The prior methods and apparatus for the transdermal administration of drugs have exhibited limited success. Accordingly, a continuing need exists in the industry for an improved device for monitoring, sampling or delivering substances.

SUMMARY OF THE INVENTION

The present invention is directed to a method and apparatus for enhancing the penetration of a penetrating device into the skin of a patient. In particular, the invention is directed to a method and apparatus for uniformly penetrating a target site of a patient for sampling, detecting or monitoring a substance in the target site or delivering a substance to the target site.

A primary object of the invention is to provide a device capable of applying tension to a target area of the skin of a patient during the penetration by a penetrating device and during the delivery, monitoring, or sampling of a substance in the target area.

Another object of the invention is to provide a medical device for stretching the skin outwardly from a target area to enable a penetrating device to penetrate the target area with less deforming of the skin by the penetrating device.

Still another object of the invention is to provide a device for enhancing the penetration of a penetrating device to deliver a pharmaceutical agent to a target area of the stratum corneum of the skin to a sufficient depth where the pharmaceutical agent can be absorbed and utilized by the body.

A further object of the invention is to provide a medical device having an array of solid or hollow needles, microtubes, blades or lancets and a skin stretching device that cooperate together to enhance the penetration of the needles, blades or lancets to a substantially uniform depth in the skin.

Another object of the invention is to provide a medical device having a cavity for receiving a substance and having a plurality of needles, blades or lancets for penetrating the stratum comeum in a target area of the skin to a substantially uniform depth for delivering the substance to the skin.

A further object of the invention is to provide a device having a substantially conical shaped shield made of a flexible material that is able to stretch the skin of a patient outwardly from a target site when the device is pressed downward onto the skin of the patient.

Another object of the invention is to provide a medical device having a conical shaped shield that is able to apply a tension to the skin and enable a substantially uniform penetration of the skin by a penetrating device.

A further object of the invention is to provide a medical device for monitoring, sampling or delivering a substance where the device includes at least two arms that extend outwardly from a housing to contact and push the skin of a patient outwardly from a target area by applying a downward pressure on the device.

A still further object of the invention is to provide a medical device having a plurality of microneedles for penetrating the stratum corneum and a device for holding a target area of the skin under tension to enable uniform penetration of the skin by the microneedles.

These and other objects of the invention are substantially attained by providing a device for stretching the surface of the skin of a patient. The device comprises a medical device for contacting the skin of a patient, and a skin stretching device which is coupled to the medical device for stretching skin of a patient away from the medical device when a downward pressure is applied on the medical device toward the skin of a patient either before or after the medical device contacts the skin.

The objects and advantages of the invention are further attained by providing a delivery device for delivering a substance intradermally to a patient. The device comprises a housing having a top wall, a bottom wall and at least one side wall enclosing a cavity for containing a substance to be delivered to a patient, and at least one skin penetrating device on the bottom wall. The bottom wall has at least one opening for supplying the substance from the cavity to the at least one skin penetrating device. A stretching device is coupled to the housing for stretching the skin of a patient in at least one dimension. The stretching device has at least one member with a first end coupled to the device and a second end spaced axially from the at least one skin stretching device and the housing, wherein the at least one member is positioned to contact the skin of a patient in at least one dimension before the skin penetrating device contacts the skin.

Another object of the invention is to provide a method of subjecting the skin of a patient to a medical device. The method comprises the steps of providing a medical device having a skin stretching device, positioning the medical device with the stretching device on the skin of a patient and applying a sufficient force on the device toward the skin where the stretching device stretches the skin away from the medical device and the medical device contacts the skin.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which.

DETAILED DESCRIPTION OF THE PREFERRED EMBODIMENTS

Figure 2:
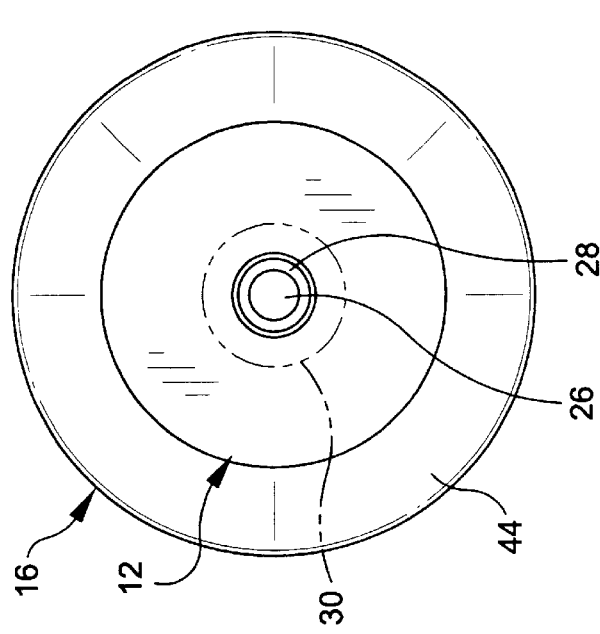
FIG. 2 is a top view of the transdermal delivery device of FIG. 1.

The present invention is directed to a medical device for monitoring, sampling or administering a substance through the skin of a patient. One aspect of the invention is directed to a device and to a method for stretching the skin of a patient in a designated or target area. More particularly, the device and method are directed to a device including a medical device, and a device for stretching the skin to enhance penetration of the skin by a skin penetrating member. The medical device can be a monitoring, sampling or delivery device.

The invention in one preferred embodiment is directed to a device having a penetrating device capable of obtaining substantially uniform penetration of the skin and to a method for penetrating the stratum corneum of the skin of a patient. As used herein, the term "penetrate" refers to entering a layer of the skin without necessarily passing completely through. "Piercing" refers to passing completely through a layer of the skin. As used herein, "transdermal" refers to the monitoring, sampling or delivery of a substance through one or more layers of skin. "Intradermal" refers to one or more layers within the skin and not limited to the dermis layer of the skin.

The device and method of the invention is primarily for enhancing the penetration by a penetrating device into the skin of a patient. The device is used in combination with a monitoring device, sampling device, delivery device or other medical device where it is necessary to penetrate the skin of a patient. The monitoring and sampling devices can be standard devices supporting a suitable penetrating device as known in the art. A delivery device having a plurality of microneedles is chosen to illustrate the various aspects of the invention, although it will be understood that the invention is not limited to delivery devices.

In preferred embodiments, the penetration enhancing device includes a penetrating device for penetrating the skin of a patient. The petetrating device can be a single member or a device having a plurality of members. Generally, the penetrating device is a plurality of solid or hollow members assembled in an array and having a length to penetrate the skin to a desired depth. The penetrating members can be solid or hollow needles, blades, microtubes, lancets, microneedles, and the like.

The penetration enhancing device of the invention is particularly suitable for penetrating devices intended to pierce the stratum corneum of the skin. It is typically difficult to obtain uniform penetration of microdevices due to the resilience of the skin. Microdevices having a length of 100 microns or less can deform the skin without penetrating the skin when pressed against the skin. Increasing the pressure of the microdevice against the skin results in penetration of some areas but generally does not provide uniform penetration of the microdevice. The penetration enhancing device of the invention stretches the skin to enable substantially uniform penetration of an array of penetrating members.

The penetration enhancing device of the invention is suitable for use with any penetrating device, but is particularly suitable for use with penetrating members having a length of about 2 mm or less. The penetration enhancing device is effective for enabling the penetration of members having a length of 10 microns to about 2000 microns. In embodiments of the invention, the penetrating members have a length of about 100 microns to about 1,000 microns.

The device and method of the invention are particularly suitable for withdrawing a sample through the skin for detection, analysis or monitoring. Examples of substances that can be sampled include various analytes, drugs and glucose. In one embodiment of the invention, the device and method are suitable for use in administering various substances, including pharmaceutical agents, to a patient, and particularly to a human patient. As used herein, a pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, adjuvants, biologics, and the like. Other substances that can be delivered intradermally to a patient include proteins, peptides and fragments thereof. The proteins and peptides can be naturally occurring, synthesized or recombinantly produced.

The invention in a first embodiment as shown in FIGS. 1–5 is directed to a device 10 having a housing 12, a skin penetrating member such as a cannula 14 and a device 16 for tensioning the skin to enable the penetrating device to penetrate the skin of a patient. For purposes of illustration, device 10 is a delivery device although the invention is not limited to delivery devices. The devices can, for example, a sampling device for withdrawing a sample from a patient or a monitoring device for monitoring a substance level in the patient. The invention is further directed to a method of delivering a substance to a patient using the delivery device 10. The embodiment of FIGS. 1–5 is intended to be exemplary of the stretching device of the invention and is not intended to be limited to delivery devices. It will be understood that the skin stretching device of the invention can be used in combination with sampling or monitoring devices.

Figure 3:
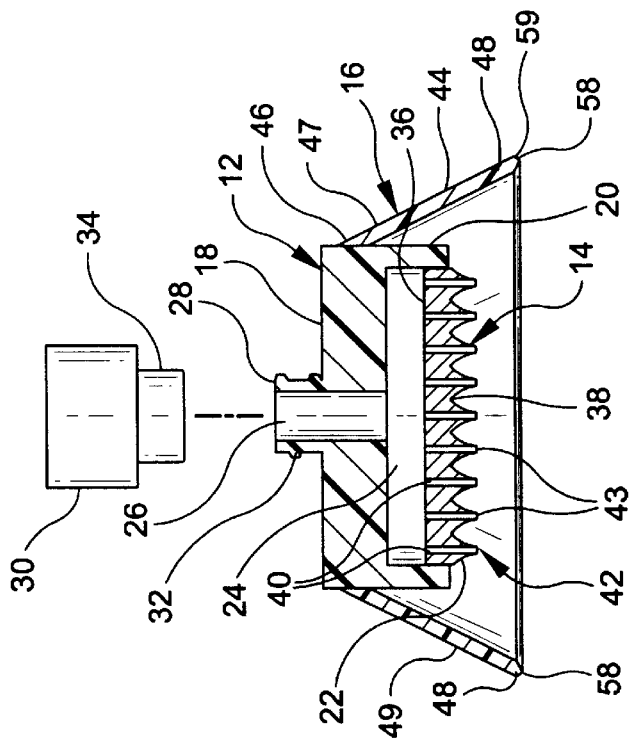
FIG. 3 is a cross-sectional view of the transdermal delivery device of FIG. 1 showing the stretching device in the normal position.

Referring to FIGS. 1-5, housing 12 has a generally cylindrical shape with a top wall 18, a side wall 20 and a bottom wall 22. As shown in FIG. 3, bottom wall 22 is spaced from top wall 18 to define a cavity 24. Top wall 18 includes a passage 26 defining an inlet to cavity 24. A collar 28 is coupled to top wall 18 and encircles passage 26 for connecting with a container 30. In the embodiment illustrated, container 30 is a supply container for delivering a substance. In embodiments where the device is a sampling device, container 30 can induce a negative pressure to withdraw the substances into the sampling device. Collar 28 in the embodiment illustrated includes external threads 32 to define a Luer-type fitting. Container 30 also includes a Luer fitting 34 for coupling with threads 32 of collar 28. In the embodiment shown, collar 28 is centrally located on top wall 18. In further embodiments, collar 28 and passage 26 can be located in another suitable position on top wall 18 or side wall 20 for connecting container 30 with cavity 24.

Bottom wall 22 is coupled to side wall 20 to form a fluid-tight seal and to enclose cavity 24. Bottom wall 22 can be coupled to side wall 20 using a suitable adhesive or by other bonding methods as known in the art. In one embodiment, top wall 18 and side wall 20 are integrally formed. In further embodiments, side wall 20 can be a separate element coupled to top wall 18 or integrally formed with bottom wall 22. Referring to FIG. 3, bottom wall 22 includes a top surface 36 facing cavity 24 and a bottom surface 38 facing outwardly from the device 10. Bottom surface 38 of bottom wall 22 defines cannula 14. A plurality of passages 40 extend through bottom wall 22 from cavity 24 to bottom surface 38.

In the embodiment illustrated, cannula 14 is an array 42 formed from a plurality of microneedles 43 arranged in rows and columns with the passages 40 extending axially through microneedles 43. In preferred embodiments, the rows and columns of microneedles 43 are uniformly spaced apart as shown in the bottom view of FIG. 4. Microneedles 43 can be spaced apart a distance of about 0.05 m to about 5 mm. In further embodiments, cannula 14 can be a single needle, multiple needles, or microtubes as known in the art. As used herein, the term cannula refers to solid or hollow microneedles, microtubes, single needles, and multiple needles that are able to penetrate the skin to a desired depth. Cannula 14 can be integrally formed with bottom wall 22 as shown or can be a separate element that is coupled to bottom wall 22. For example, cannula 14 can be a microneedle array formed from a silicon wafer or other support that is attached to a bottom wall of a delivery device. In further embodiments, cannula 14 can be needles or blades that are coupled to the bottom wall of the delivery device. For example, a bottom wall of the housing can be provided with a plurality of spaced-apart holes that extend through the bottom wall and a needle press fitted into the holes.

Figure 1:
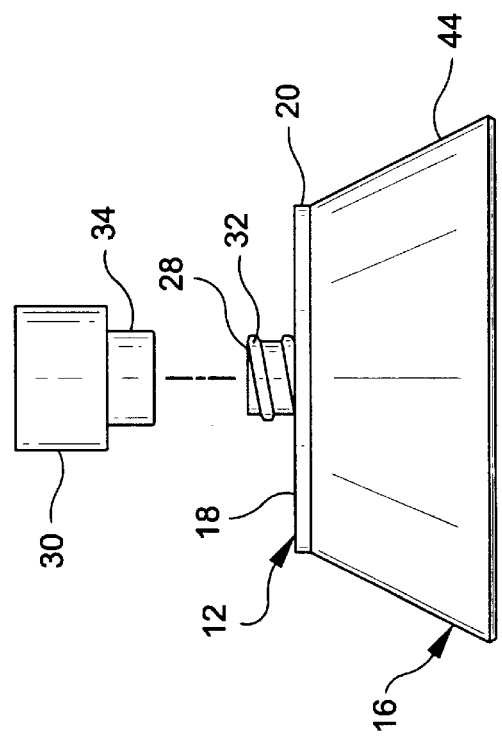
FIG. 1 is a side view of the transdermal delivery device in accordance with a first embodiment of the invention.
Figure 4:
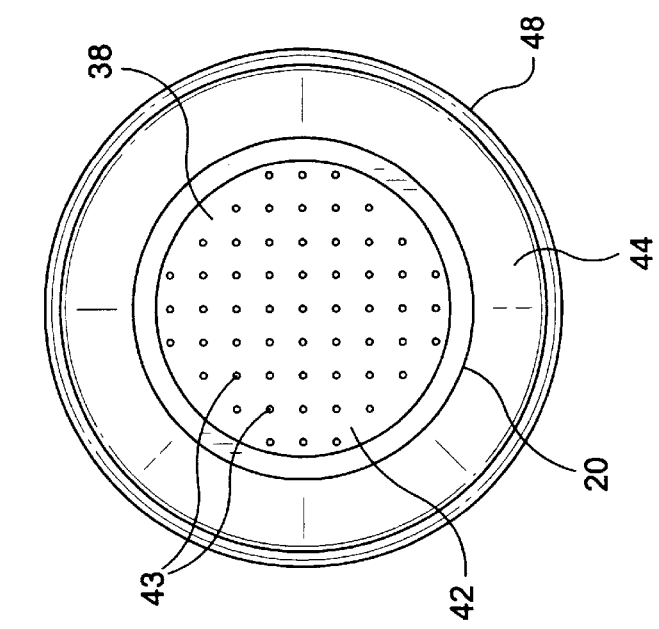
FIG. 4 is a bottom view of the transdermal delivery device of FIG. 1 showing the array of microneedles and the stretching device.

Stretching device 16 is in the form of a substantially frustoconical shaped shield 44 as shown in FIGS. 1 and 3. In the embodiment illustrated, shield 44 has a generally straight side wall that extends outwardly from housing 12 and encircles cannula 14. In further embodiments, shield 44 can have a hemispherical shape.

Shield 44 includes a first end 46 at the top edge 47 and a second end 48 at the bottom edge 49 of shield 44. First end 46 of shield 44 is coupled to housing 12 so that shield 44 completely surrounds housing 12. Shield 44 can be attached to housing 12 using various attaching methods such as, for example, adhesive bonding or welding. Alternatively, shield 44 can be integrally formed with housing 12. In preferred embodiments, shield 44 is made of a flexible plastic or rubber-like material that is able to deform and stretch when a force is applied to the shield.

As shown in FIG. 3, shield 44 is coupled to housing 12 and is flared outwardly from housing 12 in an axial direction downward toward bottom wall 22 and cannula 14. Shield 44 has a length to extend beyond cannula 14 as shown in FIG. 3. Second end 48 is spaced radially outward and axially from cannula 14. As shown in FIG. 3, second end 48 lies in a plane spaced from and substantially parallel to a plane of cannula 14 and housing 12.

Device 10 is generally made from a plastic material that is nonreactive with the substance being administered. Suitable plastic materials include, for example, polyethylene, polypropylene, polyesters, polyamides and polycarbonates as known in the art. The cannula can be made from various materials as known in the art. For example, microneedles and microtubes can be made from silicon, stainless steel, tungsten steel, alloys of nickel, molybdenum, chromium, cobalt, and titanium, ceramics, glass polymers and other non-reactive metals, and alloys thereof.

The length and thickness of the microneedles are selected based on the particular substance being administered and the thickness of the stratum corneum in the location where the device is to be applied. As shown in FIG. 3, the microneedles are substantially uniform and have a substantially uniform length. In one embodiment, the microneedles penetrate the stratum corneum substantially without penetrating or passing through the epidermis.

The microneedles can have a length for penetrating the skin up to about 2 mm and generally less than 1 mm. Suitable microneedles typically have a length of about 100 microns to about 2,000 microns. In embodiments of the invention, the microneedles can have a length of about 200 to about 1500 microns. The microneedles in the illustrated embodiment have a generally conical shape. In alternative embodiments, the skin penetrating members can be triangles, flat blades or pyramids. Typically, the skin penetrating members are perpendicular to the plane of the device and have a substantially uniform height. In embodiments where the skin penetrating members are needles, the width of the needles can be about 15 to 40 gauge to obtain optimum penetration of the skin.

Device 10 is used to withdraw a sample or deliver a substance intradermally or intraepidermally to a patient. In the embodiment illustrated, container 30 is coupled to collar 28 on housing 12 to supply a substance to cavity 24. Container 30 can be a standard syringe or unit dose device as known in the art capable of delivering a suitable dosage of a substance to a patient or withdrawing a substance from a patient. Container 30 generally delivers the substance under slight pressure to form an active delivery system. Alternatively, container 30 can provide a passive delivery system for delivering a substance over a period of minutes or hours depending on the substance being delivered and the desired rate of delivery. In the embodiment illustrated, container 30 is removably coupled to housing 12, although in further embodiments, container 30 can be integrally formed with housing 12.

Figure 5:
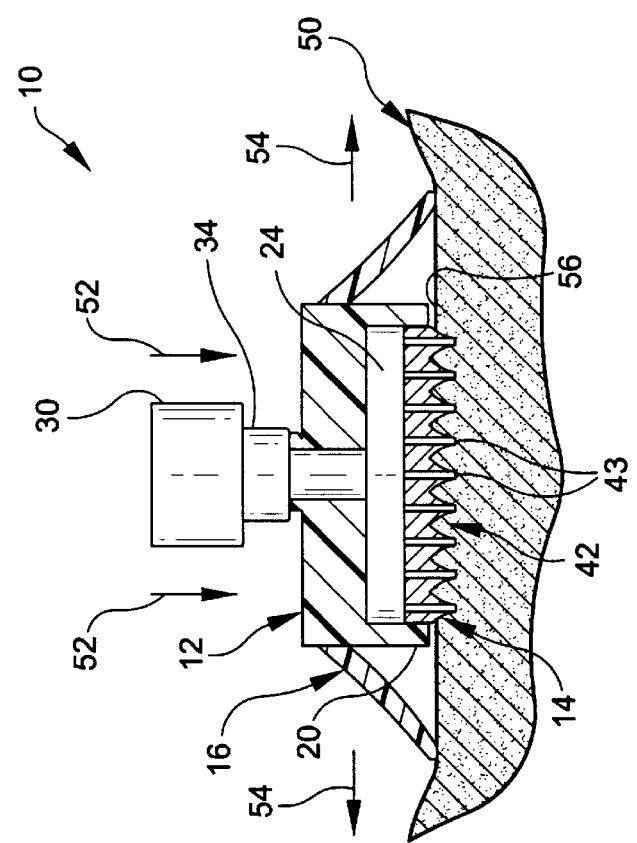
FIG. 5 is a cross-sectional side view of the embodiment of FIG. 1 showing the stretching device in the compressed position and the skin in a target area in the stretched condition.
Figure 8:
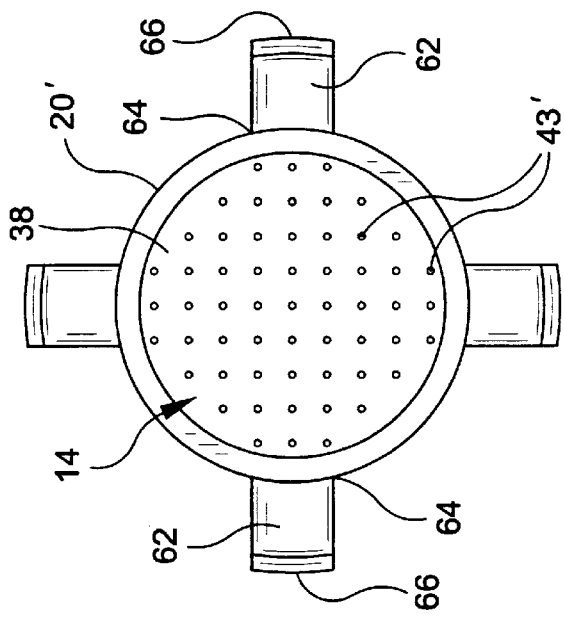
FIG. 8 is a bottom view of the embodiment of FIG. 6.
Figure 7:
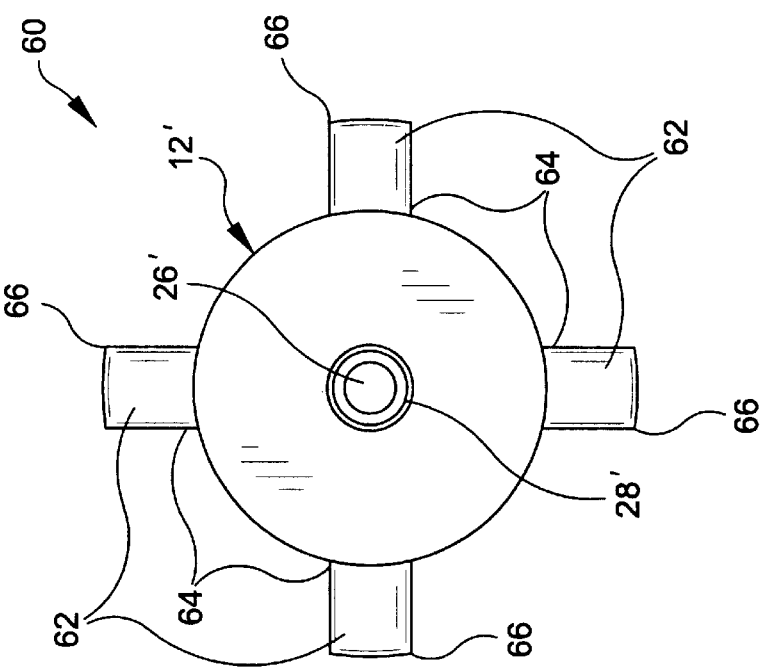
FIG. 7 is a top view of the transdermal delivery device of the embodiment of FIG. 6.

Device 10 is used by placing the device on skin 50 of a patient with second end 48 of shield 44 resting on the skin. Device 10 is then pressed downwardly against skin 50 in the direction of arrows 52 as shown in FIG. 5. The frustoconical shape of shield 44 pushes skin 50 outwardly in the direction of arrows 54 in all directions away from target site 56, thereby stretching and tensioning the skin to a taut condition. The skin stretching device can be shaped to stretch the skin in either a circular or an eliptical pattern. Pressure is applied to delivery device 10 until cannula 14 pierces skin 50 in target site 56. Stretching skin 50 in target site 56 enables cannula 14 to penetrate target site 56 rather than simply deforming the skin without penetration. As shown in FIG. 5, the downward pressure on delivery device 10 deforms shield 44 outwardly from housing 12 to push skin 50 away from target area 56. Second end 48 of shield 44 moves from the position shown in FIG. 3 where second end 48 is spaced axially from cannula 14 to the position of FIG. 5 where second end 48 is substantially in the plane of cannula 14. In the illustrated embodiment, cannula 14 is an array of microneedles where each of the microneedles is able to penetrate the skin substantially uniformly. Shield 44 can be positioned to stretch and tension skin 50 either before or simultaneously with the member contacting the skin. Once the members pierce the skin to the desired depth, a substance can be withdrawn, delivered or monitored through the skin of the patient.

Shield 44 is generally made of a resilient and elastic material having sufficient elasticity to stretch and deform when a pressure is applied to delivery device 10 without causing excessive discomfort to the patient. In the embodiment illustrated, second end 48 moves radially outward from housing 12 in a generally pivotal motion when the downward pressure is applied. In further embodiments, shield 44 can be dimensioned to buckle or fold when a downward pressure is applied, thereby producing an outward force on second end 48.

In embodiments of the invention, second end 48 of shield 44 can include a friction enhancing member to assist in pushing the skin outwardly from target site 56 encircled by shield 44. In the embodiment illustrated, second end 48 includes a rib 58 facing downwardly from housing 12 and encircling shield 44 to assist in gripping the skin and pushing the skin outwardly from cannula 14. An adhesive or tacky material, such as a pressure sensitive adhesive 59, also can be provided on second end 48 to assist in pushing the skin outwardly from cannula 14. In further embodiments, shield 44 can be made from a rubber-like material or other material having a high friction coefficient.

Embodiment of FIGS. 6–9

Referring to FIGS. 6–9, a delivery device 60 in a second embodiment of the invention is shown. Delivery device 60 is similar to the device 10 of the embodiment of FIGS. 1–5, except for the skin stretching members 62. Accordingly, identical components are identified by the same reference number with the addition of a prime.

In this embodiment, delivery device 60 includes a plurality of stretching members 62. In the embodiment illustrated, four stretching members 62 are provided that are uniformly spaced apart around housing 12' and extend in a generally outward direction from housing 12'. The four stretching members 62 enable the skin to be stretched in two dimensions in a manner similar to the embodiment of FIGS. 1–5. In further embodiments, two stretching members can be provided on opposite sides of housing 12' to stretch the skin in one dimension. Preferably, four stretching members are provided to push the skin uniformly away from the target site.

Figure 6:
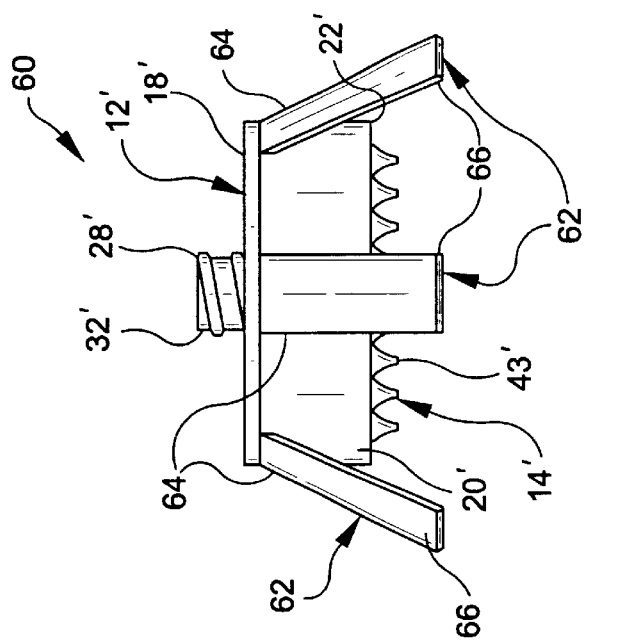
FIG. 6 is side elevational view of the delivery device in a second embodiment of the invention.

Stretching members 62 are preferably made of a flexible material having a generally rectangular shape. A first top end 64 of stretching member 62 is coupled to housing 12' adjacent top wall 18. As shown in FIG. 6, stretching members 62 extend at an incline away from housing in a direction toward bottom wall 22'. Stretching members 62 include a second bottom end 66 spaced radially from housing 12' and spaced axially from cannula 14'. Bottom end 66 has a dimension sufficient to grip the skin effectively without piercing the skin or creating extreme discomfort to the patient.

Figure 9:
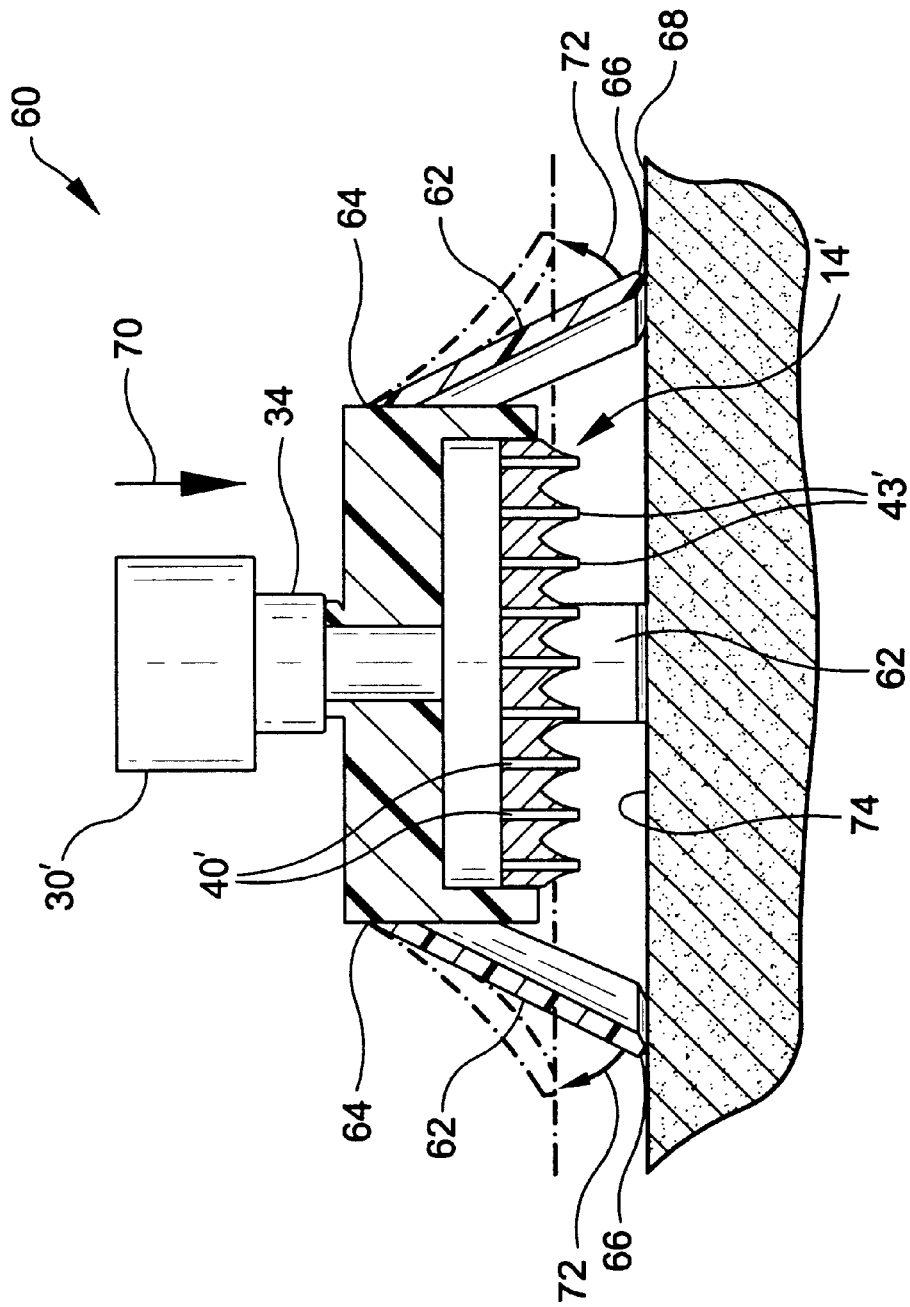
FIG. 9 is a cross-sectional side view of the embodiment of FIG. 6 showing the device in contact with the skin.

Device 60 is used in a similar manner to the device of the embodiment of FIGS. 1–5. Referring to FIG. 6, delivery device 60 is placed on the skin 68 of a patient with second end 66 of stretching member 62 resting on the skin. A supply container 30' is coupled to collar 28' as shown in FIG. 9 and device 60 is pressed against skin 68 in the direction of arrow 70. The incline of stretching members 62 and the downward pressure toward the skin 68 cause a generally pivoting motion to stretching members 62 in the direction of arrows 72 away from target area 74. The bottom ends 66 of stretching member 62 push skin 68 away from target area 74 to tension target area 74 as cannula 14' contacts target area 74. The tension applied to target area 74 enables cannula 14' to penetrate skin 68 with minimal deformation of skin 68. Supply container 30' is then actuated to dispense the contents and direct the contents through inlet 26' to cavity 24'. The contents are then directed through passages 40' to microneedles 42' and into skin 68 where the substance can be absorbed by the body.

Figure 10:
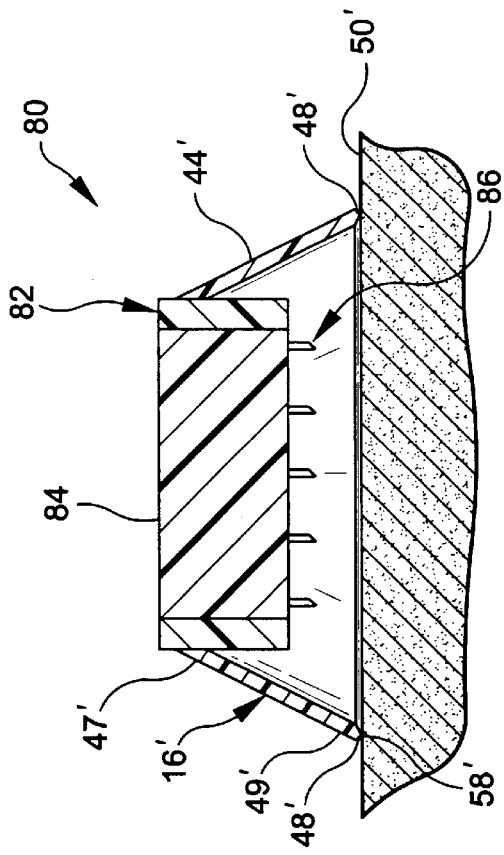
FIG. 10 is a cross-sectional side view of a device in a further embodiment of the invention.

Embodiment of FIG. 10

FIG. 10 shows another embodiment of the invention for obtaining a sample of a substance from the skin or monitoring the presence of substance in the body. The device 80 includes a stretching device similar to the embodiment of FIGS. 1–5 so that identical components are identified by the same reference number with the addition of a prime.

Referring to FIG. 10, device 80 includes a housing 82 supporting a flexible shield 44'. In this embodiment, housing 80 has a generally annular shape for supporting a medical device 84. The medical device 84 can be a monitoring device or sampling device containing an absorbing medium for absorbing substances from the skin as known in the art. In one embodiment, medical device 84 is a glucose sampling device for detecting glucose levels in the blood. Generally, medical device 84 includes one or more penetrating members 86 such as needles, blades or lancets for penetrating the skin to a desired depth.

Device 80 is used in a manner similar to the device of the embodiment of FIGS. 1–5. Device 80 is placed on the skin 50' of a patient in the selected location with shield 44' encircling the target area. A downward pressure is applied on the device so that shield 44' pushes skin 50' outwardly away from the target area and stretches skin 50' around the target area. The shield 44' is sufficiently flexible to enable medical device 84 to contact skin 50' in the target area. The skin in the target area being in a stretched condition permits substantially uniform contact of the medical device across the target area.

Figure 11:
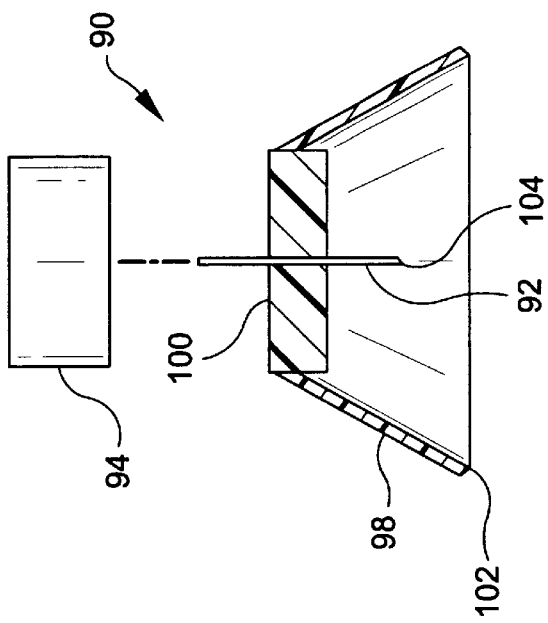
FIG. 11 is a cross-sectional side view of a device in another embodiment of the invention.

Embodiment of FIG. 11

In a further embodiment shown in FIG. 11, device 90 is a monitoring or sampling device. Device 90 in the embodiment illustrated includes a skin penetrating member 92 and a detection or monitoring device 94. Member 92 can be a probe, such as a sensor or detecting probe, for detecting the presence of and/or measuring the concentration of selected substances in the skin. A detection unit 94 is coupled to member 92 as shown in the art.

As in the previous embodiments, a skin stretching device 98 is coupled to the housing 100 and flairs outwardly from housing 100 and skin penetrating device 92. In the embodiment illustrated, skin stretching device 98 has a lower end 102 extending further from housing 100 than the tip 104 of skin penetrating member. In this manner, skin stretching device 98 contacts and stretches the skin of a patient outwardly before the skin penetrating member contacts and penetrates the skin.

Skin penetrating member 92 can be a solid probe or needle-like device for producing a suitable measuring signal that is transmitted to monitoring unit 94. Alternatively, skin penetrating member 92 is a hollow cannula for withdrawing a fluid sample and transporting the fluid to detecting or monitoring unit 94 where the sample is analyzed.

The device of the invention in one embodiment is used for active delivery of a substance and is held in place by hand pressure until the substance is delivered to the patient. In further embodiments, the delivery device is for the passive delivery of a substance and a flexible film having an adhesive on a bottom face can be attached to the housing for securing the delivery device to the skin of a patient. Preferably, the flexible film has a dimension greater than the dimension of the housing to encircle the delivery site. In still further embodiments, an area on the housing surrounding the skin penetrating member can include an adhesive for attaching the device to the skin. The adhesive layer preferably encircles the skin penetrating member and is able to form a substantially fluid tight seal around the skin penetrating member to prevent leakage of the substance and contain the substance in the target area.

In further embodiments, the device contains a diluent or carrier for a substance to be delivered to the patient. The diluent can be, for example, distilled water or saline solution. In this embodiment, a dried or lyophilized drug or pharmaceutical agent is provided that can be dissolved or dispersed in the diluent and delivered to the patient. In one embodiment, a dried drug is provided as a coating on the outer surfaces of the penetrating member. In further embodiments, the dried drug can be contained within the cavity of the housing or in the passages in a cannula.

The sampling or delivery device is produced as a complete, single use unit for delivery of a substance to a patient. The device can include a protective cover (not shown) over the microneedles to prevent damaging or contamination of the microneedles during storage and shipping. Similarly, a protective release liner can be applied over the adhesive and the device packaged in a suitable packaging material commonly used for medical devices.

While several embodiments have been shown to illustrate the present invention, it will be understood by those skilled in the art that various changes and modifications can be made therein without departing from the scope of the invention as defined in the appended claims.

What is claimed is:

1. A device for stretching the surface of the skin of a patient, said device comprising:
    a medical device for contacting the skin of a patient; and
    a skin stretching device coupled to said medical device for stretching skin of a patient away from said medical device when a downward pressure is applied on said medical device toward the skin of a patient, said stretching device having length sufficient to contact said skin of a patient prior to said medical device contacting said skin.

2. The device of claim 1, wherein said medical device is a monitoring, sampling or delivery device.

3. The device of claim 1, wherein said skin stretching device comprises a shield coupled to said medical device, said shield having a first end coupled to said medical device and a second end positioned radially outward from said medical device, wherein said shield extends at an incline with respect to said medical device.

4. The device of claim 3, wherein said shield encircles said medical device and has a substantially frustoconical shape.

5. The device of claim 4, wherein said shield is made of a flexible material, and said second end of said shield is movable from a first position to a second position spaced radially outward from said first position.

6. The device of claim 4, wherein said shield is spaced axially and radially from said medical device when in a first position and is movable to a second position where said second end is spaced radially outward from said first position.

7. The device of claim 3, wherein said shield has a length to extend beyond said medical device whereby said second end of said shield contacts the skin of a patient before said medical device contacts the skin.

8. The device of claim 7, wherein said second end of said shield is movable radially outward from said medical device by a pressure on said shield against the skin of a patient.

9. The device of claim 3, wherein said second end of said shield includes a friction enhancing member for enhancing friction between said shield and the skin of a patient.

10. The device of claim 9, wherein said friction enhancing member is an adhesive on said shield.

11. The device of claim 9, wherein said friction enhancing member is a ridge on said second end.

12. The device of claim 1, wherein said medical device includes at least one solid or hollow skin penetrating member.

13. The device of claim 1, wherein said medical device includes an array of microneedles for penetrating the skin of a patient.

14. The device of claim 13, wherein said microneedles include a hollow passage extending axially through said microneedles.

15. The device of claim 14, wherein said delivery device includes at least one skin penetrating member and a cavity for directing a substance to said at least one skin penetrating member.

16. The device of claim 12, wherein said at least one skin penetrating member has a coating of a dried or lyophilized drug.

17. The device of claim 1, wherein said stretching device comprises at least two arms for contacting the skin of a patient and stretching the skin in at least one dimension, wherein said arms have a first end coupled to said medical device and a second end spaced from said medical device, said arms being movable from a first position where said second end is spaced axially and radially from said medical device to a second position where said second end is spaced radially from said medical device and is coplanar with said medical device.

18. The device of claim 17, wherein said arms are made of a flexible material and bendable from said first position to said second position.

19. The device of claim 17, wherein said arms extend from opposite sides of said medical device for stretching skin in one dimension.

20. The device of claim 17, wherein said stretching device comprises four arms substantially uniformly spaced around said medical device.

21. A device for withdrawing, delivering or monitoring a substance through the skin of a patient, said device comprising:

a housing supporting at least one skin penetrating member for delivering a substance intradermnally to a patient; and a stretching device coupled to said housing for stretching the skin of a patient in at least one dimension, said stretching device having at least one member with a first end coupled to said device and a second end spaced axially from said housing and said at least one skin penetrating member, wherein said at least one member has a length greater than said at least one skin penetrating member and is positioned to contact and stretch the skin of a patient in said at least one dimension prior to the contact and penetration of said skin by said skin penetrating member.

22. The device of claim 21, wherein said stretching device comprises a substantially frustoconical shaped shield having a first end coupled to said housing and a second end extending axially and radially from said housing, said second end being spaced axially from said housing.

23. The device of claim 22, wherein said shield is made of a flexible material and said second end of said shield is movable from a first position to a second position spaced radially outward from said first position.

24. The device of claim 22, wherein said second end of said shield includes a friction-enhancing member.

25. The device of claim 22, wherein said friction enhancing member is an adhesive.

26. The device of claim 22, wherein said friction enhancing member is a rib.

27. The device of claim 21, wherein said stretching device comprises at least two flexible arms, each of said arms having a first end coupled to said housing and a second end diverging away from said housing, said arms having a length wherein said second end is spaced axially and radially from said cannula and said second end of said arm is movable from a first position in a plane spaced from said cannula to a second position coplanar with said cannula.

28. The device of claim 27, wherein said stretching device comprises two of said arms, each of said arms being spaced on opposite sides of said housing.

29. The device of claim 27, wherein said stretching device comprises four of said arms, each of said arms being substantially uniformly spaced apart around said housing.

30. A method of subjecting the skin of a patient to a medical device, said method comprising the steps of providing a medical device having a skin stretching device, and positioning said medical device with said stretching device on the skin of a patient and applying a sufficient force on said device toward said skin where said stretching device stretches the skin away from said medical device prior to said medical device contacting said skin.

31. The method of claim 30, wherein said medical device is a delivery device having at least one skin penetrating member, and said method further comprises delivering a substance to a patient.

32. The method of claim 30, wherein said medical device is a monitoring device and said method further comprises monitoring the level of a substance in a patient.

33. The method of claim 30, wherein said medical device is a sampling device and said method further comprises withdrawing a sample from a patient.

34. The method of claim 30, wherein said stretching device comprises at least one member with a first end coupled to said medical device and a second end spaced axially from said medical device and having a length to extend beyond said medical device, said method comprising applying a force to push said at least one member and said skin away from said medical device.

35. The method of claim 30, wherein said stretching device comprises a flexible substantially frustoconical shaped shield having a first end coupled to said medical device and a second end extending axially and radially from said medical device, and said method comprises applying sufficient pressure to cause said second end to expand radially outwardly from said medical device to stretch said skin.

36. The method of claim 30, wherein said stretching device comprises at least two flexible arms, each of said arms having a first end coupled to said medical device and a second end diverging away from said medical device, said arms having a length wherein said second end is spaced axially and radially from said medical device and said second end of said arm is movable from a first position in a plane spaced from said medical device to a second position in a plane with said medical device, and said method comprises applying sufficient pressure to said device to cause said arms to flair radially outward from said medical device to stretch said skin.

37. The method of claim 36, wherein said stretching device comprises at least four arms spaced around said medical device, said method comprising applying a force onto said medical device to force said arms outwardly from said medical device.

* * * * *